United States Patent
Judkins et al.

(10) Patent No.: US 9,750,945 B2
(45) Date of Patent: Sep. 5, 2017

(54) NEUROSTIMULATION PROGRAMMERS WITH IMPROVED RF ANTENNA RADIATION PATTERNS

(75) Inventors: James G. Judkins, Campbell, CA (US); Richard W. O'Connor, Redwood City, CA (US)

(73) Assignee: ST. JUDE MEDICAL LUXEMBOURG HOLDINGS SMI S.A.R.L., Luxembourg (LU)

( * ) Notice: Subject to any disclaimer, the term of this patent is extended or adjusted under 35 U.S.C. 154(b) by 1113 days.

(21) Appl. No.: 12/893,946

(22) Filed: Sep. 29, 2010

(65) Prior Publication Data

US 2012/0029599 A1    Feb. 2, 2012

Related U.S. Application Data

(60) Provisional application No. 61/369,988, filed on Aug. 2, 2010.

(51) Int. Cl.
| | | |
|---|---|---|
| A61N 1/372 | (2006.01) | |
| H01Q 1/24 | (2006.01) | |
| H01Q 9/04 | (2006.01) | |
| H01Q 9/42 | (2006.01) | |
| H01Q 13/10 | (2006.01) | |

(52) U.S. Cl.
CPC ..... *A61N 1/37229* (2013.01); *A61N 1/37235* (2013.01); *H01Q 1/243* (2013.01); *H01Q 9/0407* (2013.01); *H01Q 9/42* (2013.01); *H01Q 13/10* (2013.01)

(58) Field of Classification Search
CPC ............ A61N 1/37211; A61N 1/37217; A61N 1/37223; A61N 1/37229; A61N 1/37235

USPC ............. 607/32, 60; 128/903; 343/702, 846
See application file for complete search history.

(56) References Cited

U.S. PATENT DOCUMENTS

| | | | |
|---|---|---|---|
| 5,759,199 A * | 6/1998 | Snell et al. ............... | 607/60 |
| 6,167,312 A * | 12/2000 | Goedeke ................. | 607/60 |
| 6,240,317 B1 | 5/2001 | Villaseca et al. | |
| 6,249,703 B1 | 6/2001 | Stanton et al. | |
| 6,317,099 B1 | 11/2001 | Zimmerman et al. | |
| 6,392,610 B1 | 5/2002 | Braun et al. | |
| 6,985,088 B2 | 1/2006 | Goetz et al. | |

(Continued)

OTHER PUBLICATIONS

Foegelle, "Antenna Pattern Measurement: Concepts and Techniques," Compliance Engineering Magazine, http://www.ce-mag.com/archive/02/Spring/fogelle1.html, Spring 2002, 32 pages.

(Continued)

*Primary Examiner* — Eugene T Wu
(74) *Attorney, Agent, or Firm* — Vierra Magen Marcus LLP

(57) ABSTRACT

To provide for an improvement in the communication between an external handheld programmer and an implantable pulse generator (IPG) implanted within a patient or an external pulse generator attached to the patient, an antenna of the programmer is positioned relative to the ground plane of the programmer such that when a person handholds the programmer in its predetermined intended orientation a radiation pattern produced by the antenna has substantially maximum RF radiation generally directed toward the patient, regardless whether the person that handholds the programmer is the patient or another person located near the patient.

15 Claims, 12 Drawing Sheets

(56) References Cited

U.S. PATENT DOCUMENTS

| | | | |
|---|---|---|---|
| 7,146,219 B2 | 12/2006 | Sieracki et al. | |
| 7,203,549 B2 | 4/2007 | Schommer et al. | |
| 7,263,406 B2 | 8/2007 | Toy et al. | |
| 7,272,445 B2 | 9/2007 | Phillips et al. | |
| 7,289,855 B2 | 10/2007 | Nghiem et al. | |
| 7,356,369 B2 | 4/2008 | Phillips et al. | |
| 7,554,493 B1 | 6/2009 | Rahman | |
| 7,561,921 B2 | 7/2009 | Phillips et al. | |
| 7,729,766 B2 | 6/2010 | Toy et al. | |
| 7,777,480 B2 | 8/2010 | Wolfe | |
| 8,629,761 B2* | 1/2014 | Ljungstrom et al. | 340/10.1 |
| 2003/0157903 A1 | 8/2003 | Begic | |
| 2003/0222823 A1* | 12/2003 | Flint et al. | 343/702 |
| 2004/0138725 A1* | 7/2004 | Forsell | 607/61 |
| 2005/0075692 A1* | 4/2005 | Schommer et al. | 607/60 |
| 2006/0061512 A1* | 3/2006 | Asano et al. | 343/702 |
| 2006/0142820 A1* | 6/2006 | Von Arx et al. | 607/60 |
| 2008/0172109 A1* | 7/2008 | Rahman et al. | 607/60 |
| 2010/0066500 A1* | 3/2010 | Ljungstrom et al. | 340/10.1 |
| 2010/0318159 A1* | 12/2010 | Aghassian et al. | 607/59 |
| 2010/0324620 A1* | 12/2010 | Libbus et al. | 607/10 |

OTHER PUBLICATIONS

International Search Report and Written Opinion for PCT/US2011/044887, mailed Nov. 30, 2011.

King-Hunter et al., "Model 37742 Patient Programmer: Pain Therapy User Manual", Medtronic, Oct. 13, 2004, Part No. 220907005, rev. B.

Notification Concerning Transmittal of International Preliminary Report mailed Feb. 14, 2013, in International Appl. No. PCT/US2011/44887 filed Jul. 21, 2011.

\* cited by examiner

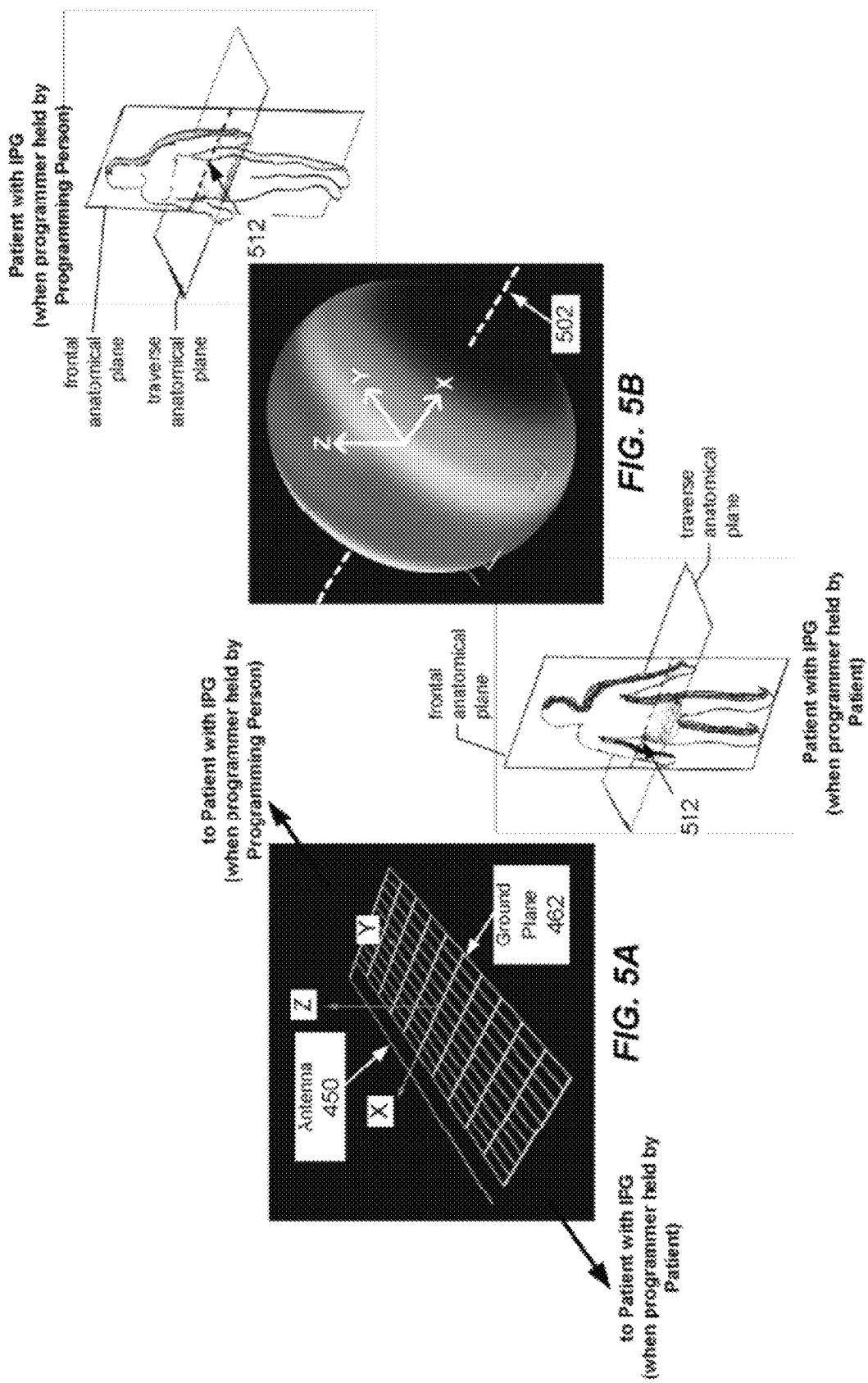

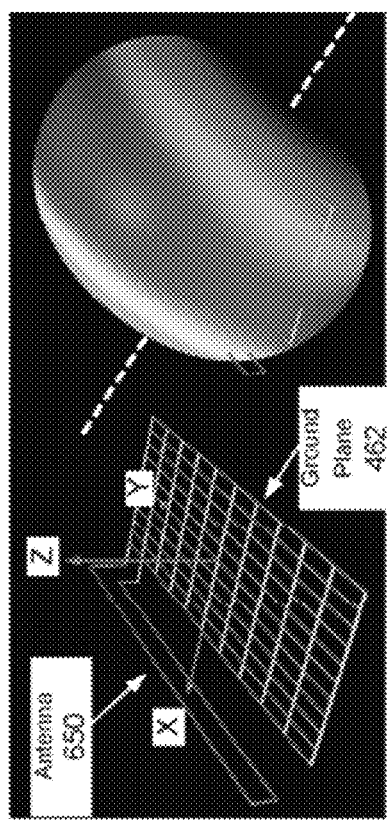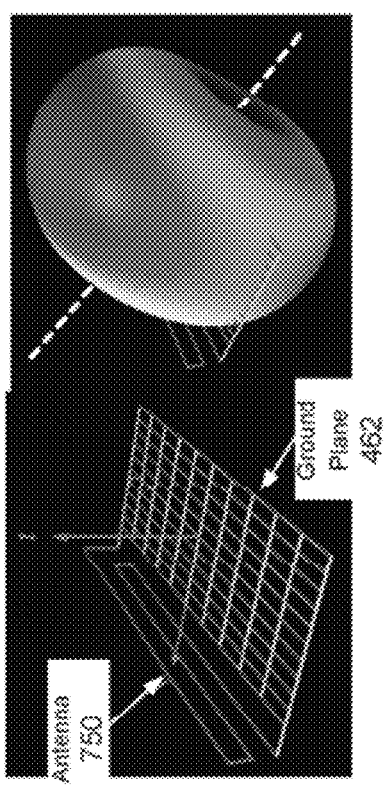
FIG. 6A  FIG. 6B  FIG. 7A  FIG. 7B

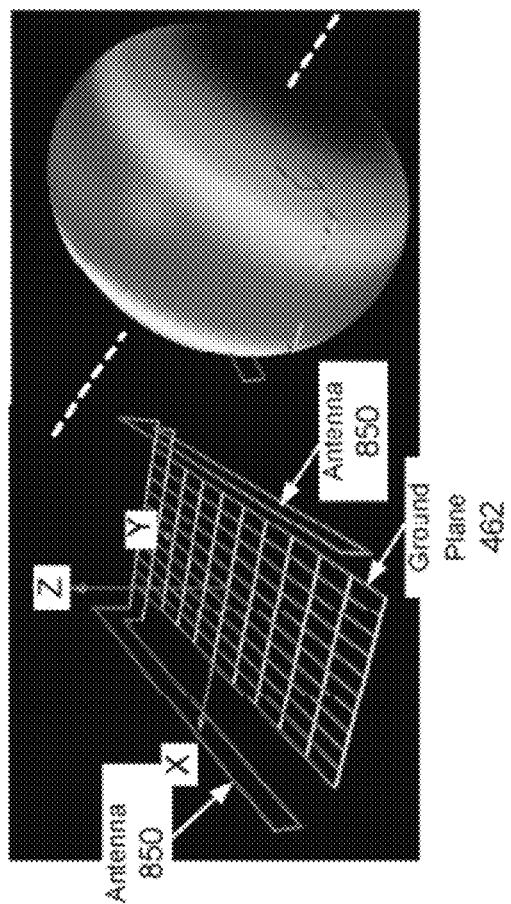

NEUROSTIMULATION PROGRAMMERS WITH IMPROVED RF ANTENNA RADIATION PATTERNS

PRIORITY CLAIM

The present application claims priority under 35 U.S.C. 119(e) to U.S. Provisional Patent Application No. 61/369,988, entitled NEURO STIMULATION PROGRAMMERS WITH IMPROVED RF ANTENNA RADIATION PATTERNS, filed Aug. 2, 2010, which is incorporated herein by reference.

FIELD OF THE INVENTION

Embodiments of the present invention generally relate to methods, devices and systems that are used to communicate with pulse generators that are used to treat pain or other conditions.

BACKGROUND OF THE INVENTION

Neurostimulation has become an accepted treatment for patients with chronic pain in their back and/or limbs who have not found pain relief from other treatments. In general, neurostimulation comprises applying an electrical current to nerve tissue in the pathway of the chronic pain. This creates a sensation that blocks the brain's ability to sense the previously perceived pain. There are two conventional forms of electrical stimulation commonly used to treat chronic pain: Spinal Cord Stimulation (SCS) and Peripheral Nerve Field Stimulation (PNFS). In SCS, electrical leads are placed along the spinal cord. A programmable implantable pulse generator (IPG) is implanted in the upper buttock or abdomen (under the skin) which emits electrical currents to the spinal cord via electrodes of the leads. Peripheral nerve field stimulation is similar to spinal cord stimulation, however peripheral nerve field stimulation involves placing the leads just under the skin in an area near to the peripheral nerves involved in pain.

FIGS. 1A and 1B will now be used to illustrate how an external handheld programmer (often referred to herein as an "external programmer" or simply as a "programmer") can be used to program and otherwise control an IPG. Referring to FIG. 1A, an IPG 112 is shown as being implanted within a patient 102. One or more leads 114, each having one or more electrodes 116, are connected to the IPG 112 for delivery of neurostimulation (e.g., spinal cord stimulation) to the patient. The electrode(s) 116 can be electrically coupled to electronic circuitry within the IPG 112 by coupling the leads 114 to connectors of the IPG 112. Where a housing (also referred to as the "case" or "can") of the IPG 112 is electrically conductive, the housing can act as an electrode. Although not limited thereto, the lead 114 can be positioned so that the electrodes are disposed on or near a dorsal root or dorsal root ganglion. Additional details regarding such stimulation are provided in U.S. Pat. No. 7,450,993, entitled "Methods for Selective Stimulation of a Ganglion", and U.S. patent application Ser. No. 12/607,009, entitled "Selective Stimulation Systems and Signal Parameters for Medical Conditions", both of which are incorporated herein by reference.

FIG. 1A also shows an external handheld programmer 122 that can be used to program and/or otherwise control the IPG 112. There are generally two types of programmers, both of which can be handheld and capable of wireless communication with the IPG 112. One type of programmer 122, that is used by a representative of the IPG manufacturer, a clinician, a physician and/or other medical personnel (collectively referred to hereafter as a "programming person"), is often referred to as a "clinician programmer". FIG. 1A illustrates a programming person 104 holding the programmer 122, which can be a clinician programmer. The other type of programmer 122 is often referred to as a "patient programmer" because it is primarily intended to be controlled by the patient within which the IPG is implanted. FIG. 1B illustrates the patient 102 holding the programmer 122, which can be a patient programmer. While a clinician programmer is typically more complex and typically has greater capabilities than a patient programmer, for the purpose of this discussion both types of programmers can be referred to interchangeably.

The programming of the IPG 112 performed using a clinician programmer can include identifying and storing one or more neurostimulation parameter sets that treat a targeted pain of a patient. This often requires the interaction of the programming person 104 and the patient 102. Typically while handholding the programmer 122, e.g., as shown in FIG. 1A, the programming person 104 manually adjusts the various stimulus parameters via a user interface of the programmer 122. Such a user interface is usually associated with a front surface of the programmer, but that is not to say that some buttons or the like may also be located on other surfaces of the programmer (e.g., the left or right sides). The patient 102 can give feedback (e.g., verbal feedback) to the programming person 104 as the programming person 104 cycles through the parameters. For example, after each parameter change made by the programming person 104, the programming person 104 may ask the patient 102 for efficacy feedback.

Each such neurostimulation parameter set that is programmed can define electrode parameters and neurostimulation signal parameters. The electrode parameters of each neurostimulation parameter set can define which electrodes are used to provide neurostimulation. Additionally, the electrode parameters of each neurostimulation parameter set can define which one or more electrodes used to provide neurostimulation are connected as a cathode, and which one or more electrodes used to provide neurostimulation are connected as an anode. The neurostimulation signal parameters of each neurostimulation parameter set can define a value for each of pulse width, pulse amplitude and pulse repetition rate, but are not limited thereto.

The programmer 122 (whether a clinician or patient type programmer) can also be used to select among a plurality of different stored neurostimulation parameter sets. Additionally, the programmer 122 can also be used to adjust neurostimulation signal parameters, e.g., to increase or decrease pulse amplitudes. For example, as shown in FIG. 1B, the patient 102 can hold a patient programmer type external programmer 122 in their hands, and use buttons, or the like, to select a specific neurostimulation parameter set and adjust the pulse amplitude corresponding to the selected set.

The programmer 122 will most likely communicate with the IPG 112 using the Medical Implant Communication Service (MICS) standard, which was defined by the U.S. Federal Communications Commission (FCC) and European Telecommunications Standards Institute (ETSI). The MICS standard uses a frequency band between 402 and 405 MHz to provide for bi-directional radio communication with medical implants, such as the IPG 112. The maximum transmit power allowed by the MICS standard is very low, with the maximum allowed equivalent isotropically radiated power (EIRP) being only 25 microwatts, in order to reduce the risk of interfering with other users of the same band. The MICS standard gives a maximum range of a couple of meters. By contrast, the maximum EIRP allowed for mobile phones and other mobile devices is typically orders of magnitude greater than the maximum EIRP allowed by the MICS standard.

The programmer 122 is typically designed so that a person handholding the programmer can properly view and interact with the user interface of the programmer when the programmer is handheld in its predetermined intended orientation, e.g., handheld at any angle between when a front surface (with which the user interface is associated) of the programmer is generally parallel to the ground (as in FIGS. 1A and 1B) and generally perpendicular to the ground. For example, referring position a in FIG. 1C, if the person were to handhold the programmer 122 at about waist level, the person may handhold the programmer so that the front surface of the programmer (and thus the user interface associated with the front surface) is facing upward and generally parallel to the earth's surface. For another example, referring position e in FIG. 1C, if the person were to handhold the programmer 122 at about eye level, the person may handhold the programmer so that the front surface of the of the programmer (and thus the user interface associated with the front surface) is facing sideways and generally perpendicular to the earth's surface. Still referring to FIG. 1C, the person may alternatively handhold the programmer 122 at other positions (e.g., positions b, c or d) that result in the front surface of the programmer (and thus the user interface associated with the front surface) being somewhere between parallel to the earth's surface and perpendicular to the earth's surface. So long as a person handholds the programmer such that the front surface of the housing is at any angle between and inclusive of parallel to the earth's surface and perpendicular to the earth's surface, which enables the person to view and interact with the user interface of the programmer in the predetermined intended manner, the programmer can be said to be handheld in its predetermined intended orientation. In other words, the predetermined intended orientation of the programmer can encompass a range of positions at which the programmer is intended to be held for use in its intended manner. It is also noted that the person may rest the handheld programmer on their lap, on a table, or on any other surface rather than handholding to device wherein such positioning of the device enables the person to view and interact with the user interface of the programmer in the predetermined intended manner.

Reference will now be made to FIG. 2, which illustrates an exemplary housing 252 of the programmer 122, with a front of the housing removed so that some components located within the housing 252 can be viewed. Referring to FIG. 2, a single or multilayered printed circuit board (PCB) 254 is located within the housing 252. While not shown, integrated circuits (ICs), also known as chips, and/or discrete circuitry can be attached to the PCB 254 and can be interconnected as appropriate by traces, vias and/or other conductors. One of the layers of the multilayered PCB 254 can be substantially covered with a conductor, e.g., copper or some other metal, to provide a ground plane 262 for the circuitry and an antenna 250 of the external programmer 122.

FIG. 2 shows an exemplary form factor and a typical location for the antenna 250 of an external handheld programmer relative to the ground plane 262. Referring to FIG. 2, the antenna 250 is shown as a being located in the same plane as the ground plane 262 above an upper boundary of the ground plane 262 (generally along the top of the housing 252), extending from the left side of the housing 252 to the right side of the housing 252. While in FIG. 2 the antenna 250 is shown as a conductive trace having a generally square wave shape, the radiation pattern of the antenna 250 would be substantially the same as if the conductive trace were a straight wire extending from left to right above the upper boundary of the ground plane 262. This is because the square wave shape mainly has the effect of only adding to the length of the antenna 250, which affects the frequency of signals emitted by the antenna, but does not affect the radiation pattern. For this reason, for the purpose of analyzing the radio frequency (RF) radiation pattern of the antenna 250, the antenna 250 can be considered a straight wire that extends above the top boundary of the ground plane from the left side to the right side of the housing 252, as shown in FIG. 3A.

Referring now to FIG. 3A, the rectangular grid represents the PCB ground plane 262 introduced in FIG. 2. The wire parallel to extending above the top boundary of the ground plane 262 in FIG. 3A represents the antenna 250 introduced in FIG. 2. FIG. 3B illustrates the antenna radiation pattern corresponding to FIG. 3A, i.e., the radiation pattern that results when the antenna 250 is located above the top boundary of the ground plane 262. As can be appreciated from FIG. 3B, when a person handholds the external programmer 122 in its predetermined intended orientation so that the person can properly view and interact with the user interface of the external programmer 122, the maximum RF radiation (which is represented by toroidal or donut shape) is not directed toward the IPG implanted within the patient. Rather, RF radiation nulls (i.e., the minimum radiation) occur in the direction of the IPG. Thus, when a programming person 104 handholds the programmer 122 in its intended orientation there is a RF radiation null in the direction of the patient 102, potentially resulting in poor communication with the IPG 112 implanted within the patient 102. Similarly, when a patient 102 within which the IPG 112 is implanted holds the programmer 122 in its intended orientation to select a neurostimulation parameter set or adjust a neurostimulation parameter, there is also a RF radiation null in the direction of the patient 102, again potentially resulting in poor communication with the IPG 112. The inefficient and potentially ineffective use of the radiation pattern shown in FIG. 3A for communicating with an IPG is compounded by the fact that the maximum transmit power allowed by the MICS standard is very low, as was explained above.

SUMMARY OF THE INVENTION

Specific embodiments of the present invention are related to a handheld external programmer adapted to wirelessly communicate with an IPG implanted within a patient, where the programmer has a predetermined intended orientation that specifies how a person should handhold the programmer so that the person can view and interact with a user interface of the programmer in a predetermined intended manner. In accordance with specific embodiments, the programmer includes a ground plane, a power supply and a telemetry transceiver. The telemetry transceiver is powered by the power supply and grounded by the ground plane. Additionally, the programmer includes an antenna electrically connected to the telemetry transceiver, e.g., by a coaxial cable or other transmission line. The telemetry transceiver and the antenna allow for wireless communication between the programmer and the IPG implanted within the patient. The telemetry transceiver and the antenna can alternatively allow for wireless communication between the programmer and an external pulse generator, e.g., a trial neurostimulator (TNS), attached to the patient.

To provide for improved communication between the programmer and the IPG (or an external pulse generator attached to the patient), the antenna is positioned relative to the ground plane such that when the person handholds the programmer in its predetermined intended orientation a radiation pattern produced by the antenna has substantially maximum RF radiation and substantially maximum gain generally directed toward the patient, regardless whether the person that handholds the programmer is the patient or another person located near the patient (e.g., a programming person within a few meters of the patient). As will be appreciated from the description herein, in accordance with specific embodiments this is achieved by positioning the antenna relative to the ground plane such that when the person handholds the programmer in its predetermined intended orientation the radiation pattern produced by the antenna has a generally toroidal shape having an axis of rotation parallel to the horizontal width (i.e., the axis between the left and right sides) of the programmer. Stated another way, when the person handholds the programmer in its predetermined intended orientation the radiation pattern produced by the antenna has a generally toroidal shape having an axis of rotation such that a plane generally perpendicular to the axis of rotation intersects the patient, regardless whether the person that handholds the programmer is the patient or another person located near the patient (e.g., a programming person within a few meters of the patient).

In accordance with specific embodiments, to achieve the desired antenna radiation pattern, when the person handholds the programmer in its predetermined intended orientation, the antenna is located left of the ground plane and/or right of the ground plane.

In accordance with certain embodiment of the present inventions, the ground plane is a conductive surface on a printed circuit board (PCB) located within the housing, and the antenna is a conductive trace on the same PCB, or on a separate PCB. In other embodiments, the antenna need not be a trace on a PCB.

This summary is not intended to summarize all of the embodiments of the present invention. Further and alternative embodiments, and the features, aspects, and advantages of the embodiments of invention will become more apparent from the detailed description set forth below, the drawings and the claims.

BRIEF DESCRIPTION OF THE DRAWINGS

FIG. 5A provides a representation of the ground plane and antenna shown in FIG. 4, and the antenna's relative location to the ground plane.

FIG. 5B illustrates the antenna radiation pattern for the ground plane and antenna combination shown in FIGS. 4 and 5A.

FIG. 6A illustrates a representation of a ground plane and an antenna, and the antenna's relative location to the ground plane, according to an embodiment of the present invention.

FIG. 6B illustrates the antenna radiation pattern for the ground plane and antenna combination shown in and 6A.

FIG. 7A illustrates a representation of a ground plane and an antenna, and the antenna's relative location to the ground plane, according to an embodiment of the present invention.

FIG. 7B illustrates the antenna radiation pattern for the ground plane and antenna combination shown in and 7A.

FIG. 8A illustrates a representation of a ground plane and an antenna, and the antenna's relative location to the ground plane, according to an embodiment of the present invention.

FIG. 8B illustrates the antenna radiation pattern for the ground plane and antenna combination shown in and 8A.

DETAILED DESCRIPTION OF THE INVENTION

Specific embodiments of the present invention are directed to handheld external programmers that provide for improved communications with implanted IPGs. Such embodiments are very useful when considering the fact that the maximum transmit power allowed by the MICS standard for communications between such a programmer and an implanted IPG is very low, as explained above. More specifically, the maximum allowed EIRP for communication between an external handheld programmer and an IPG is only 25 microwatts.

Figure 4:
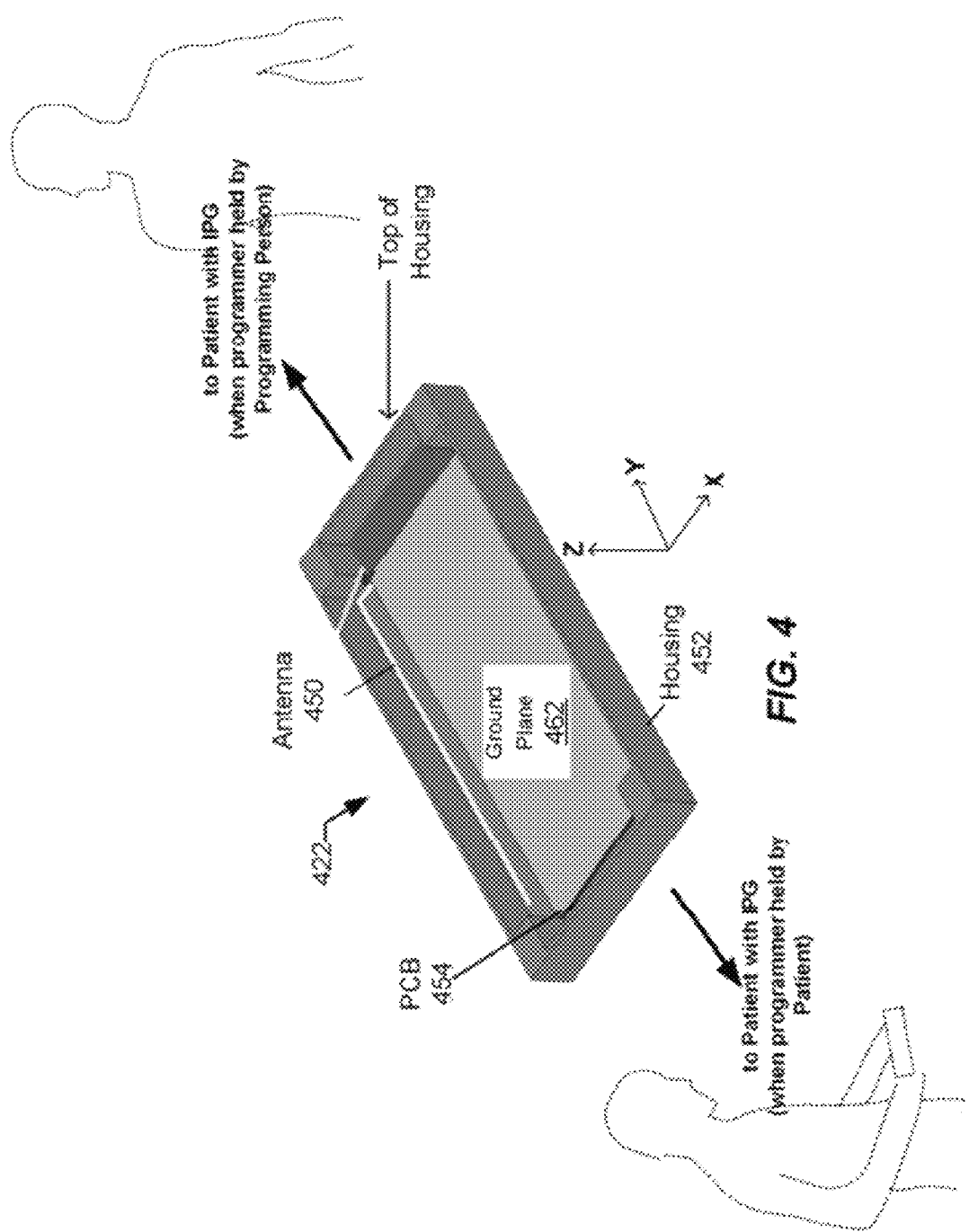
FIG. 4 illustrates exemplary form factors of a housing, a ground plane and an antenna of an external programmer, according to an embodiment of the present invention.

Specific embodiments of the present invention will now be described with reference to FIGS. 4, 5A and 5B. Referring first to FIG. 4, portions of a handheld external programmer 422 are shown, where the programmer is adapted to wirelessly communicate with an IPG implanted within a patient. The programmer 422 has a predetermined intended orientation that specifies how a person should handhold the programmer so that the person can view and interact with a user interface of the programmer in a predetermined intended manner. The user interface (e.g., 942 in FIG. 9) can include a display, buttons, a touch screen, a keypad, a graphical user interface (GUI), one or more peripheral pointing devices (e.g., a mouse, touchpad, joystick, trackball, etc.), and/or the like, but is not limited thereto. More generally, the user interface enables a patient and/or programming person to interact with the programmer 422 in an intended manner.

The predetermined intended orientation of the programmer 422 can specify, for example, that when a person handholds the programmer 422 in its predetermined intended orientation, the front surface of the housing (which has been removed in FIG. 4 to show inside the housing) can be at any angle between and inclusive of parallel to the earth's surface and perpendicular to the earth's surface, which enables the person to view and interact with the user interface of the programmer in the predetermined intended manner. This was explained above with reference to FIG. 1C. Most, if not all, of a user interface can be associated with the front surface of the housing. However, there can also be some buttons, switches and/or other components of the user interface that can be associated with other surfaces (e.g., the top surface, bottom surface, back surface, left surface and/or right surface) of the housing. For an example, an on/off switch may be associated with the left surface of the housing. Where a programming person handholds the programmer, the programming person will generally face toward the patient when holding the programmer in its predetermined intended orientation. Where the patient handholds the programmer, the patient will generally hold the programmer such that an axis between the left and right sides of the programmer is generally parallel to the traverse anatomical plane of the patient (an example of the traverse anatomical plane of a patient is shown in FIG. 5B, along with an example of the frontal anatomical plane, and an intersection 512 of these two planes).

The programmer 422 is shown as including an exemplary housing 452, with the front of the housing removed so that some components located within the housing 452 can be viewed. Located within the housing 452 is a ground plane 462. Although not specifically shown in FIG. 4, a power supply and a telemetry transceiver can also be located within the housing. Exemplary details of the power supply and the telemetry transceiver are described below with reference to FIG. 10. Still referring to FIG. 4, also located within the housing is an antenna 450, which is electrically connected to the telemetry transceiver, e.g., by a coaxial cable or other transmission line.

Figure 2:
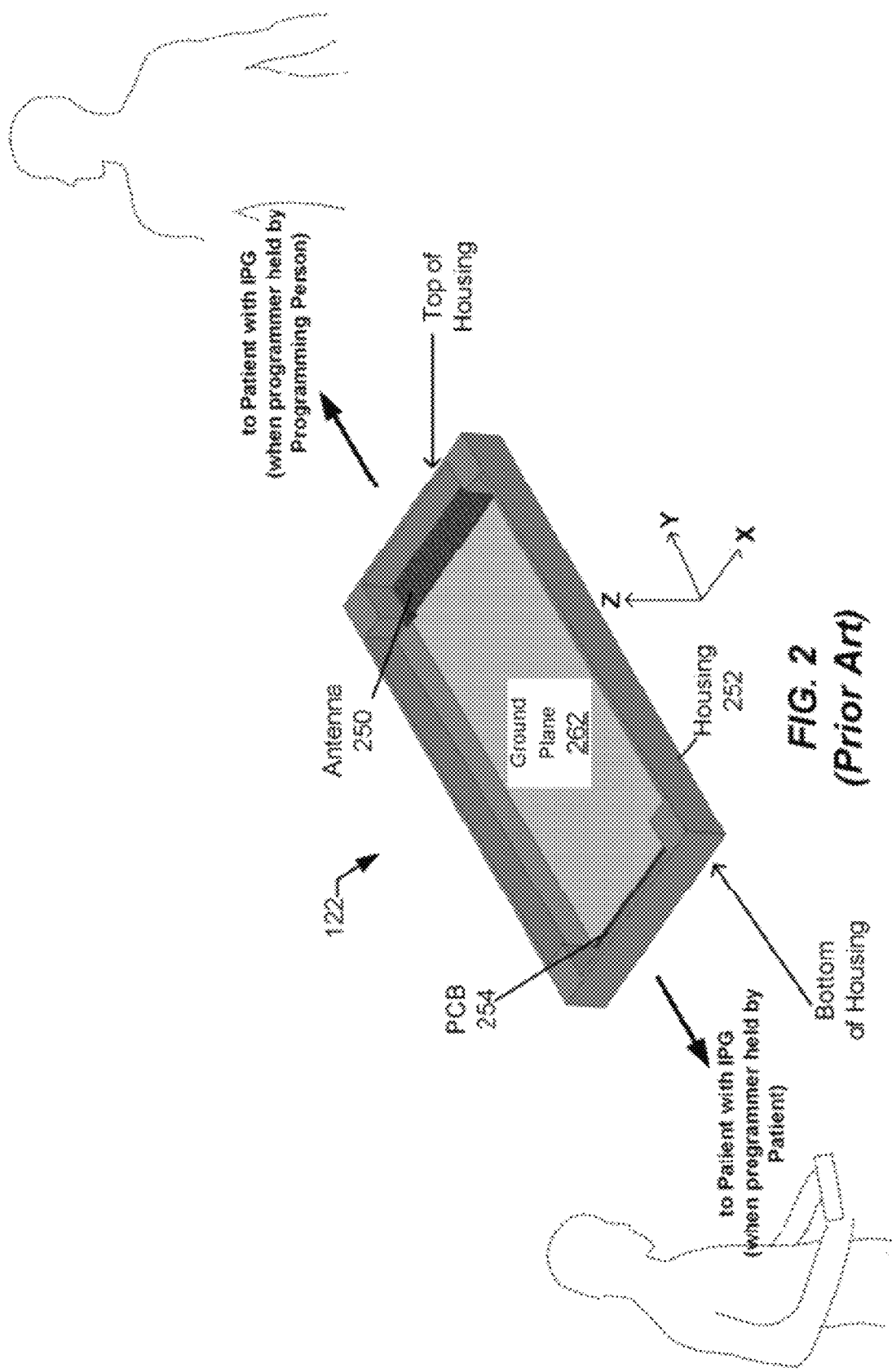
FIG. 2 illustrates exemplary conventional form factors of a housing, a ground plane and an antenna of an external programmer.
Figure 3:
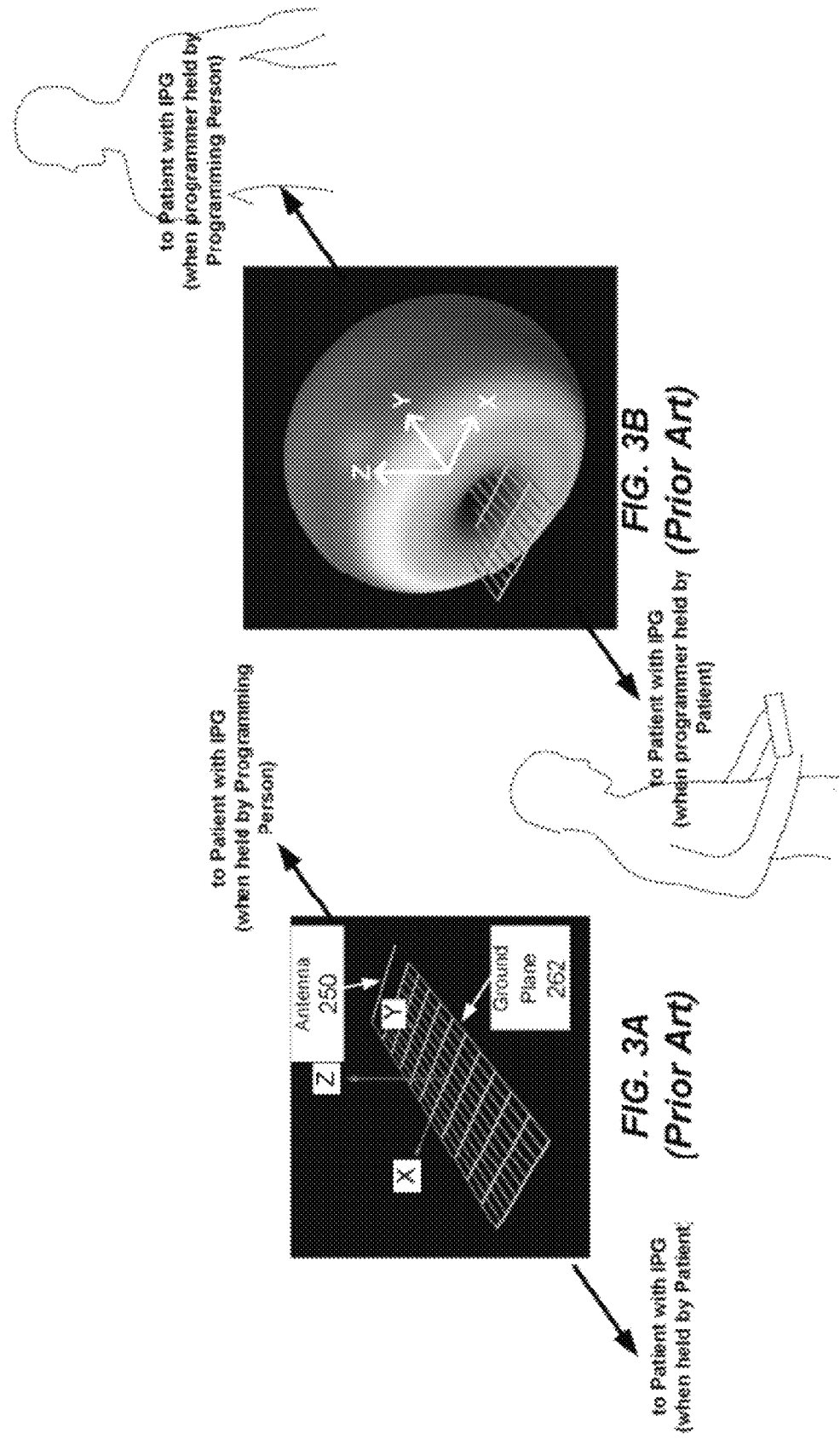
FIG. 3A provides a representation of the ground plane and the antenna shown in FIG. 2, and the antenna's relative location to the ground plane.
FIG. 3B illustrates the antenna radiation pattern for the ground plane and antenna combination shown in FIGS. 2 and 3A.

A distinction between the programmer 122 discussed above with reference to FIG. 2, and the programmer 422 introduced in FIG. 4, is the location of the antenna relative to the ground plane. More specifically, in FIG. 4 the antenna 450 is shown as being located to the left of a left boundary of the ground plane 462 (in the same plane as the ground plane 462) when a person handholds the programmer in its predetermined intended orientation. By contrast, in FIG. 2, the antenna was shown as being located above a top boundary of the ground plane 262 (in the same plane as the ground plane 262). As was discussed above with reference to FIGS. 2, 3A and 3B, when the antenna was located above a top boundary of the ground plane, there was a RF radiation null in the direction of the patient within which an IPG is implanted, regardless of whether the patient or a programmer person was handholding the programmer. This resulted in potentially poor communication between the programmer and the IPG within the patient. By contrast, locating the antenna as shown in FIG. 4 provides for improved communication between the programmer and an IPG implanted within a patient, as will now be explained with reference to FIGS. 5A and 5B.

Referring now to FIG. 5A, the rectangular grid represents the PCB ground plane 462 introduced in FIG. 4. The wire parallel to and located to the left of the left boundary of the ground plane 462 in FIG. 5A represents the antenna 450 introduced in FIG. 4. Unless stated otherwise, locative terms such as left, right, top, bottom, and the like, are relative to the visual perspective of the person holding the programmer in its predetermined intended orientation, regardless whether the person that handholds the programmer is the patient within which the IPG is implanted or another person (e.g., a programming person) located near the patient.

FIG. 5B illustrates the antenna radiation pattern corresponding to FIG. 5A, i.e., the radiation pattern that results when the antenna 450 is located to the left of the ground plane 462 (i.e., to the left of the left boundary of the ground plane) when a person handholds the programmer in its predetermined intended orientation. As can be appreciated from FIG. 5B, the antenna 450 is positioned relative to the ground plane 462 such that when the person handholds the programmer in its predetermined intended orientation the radiation pattern produced by the antenna has a generally toroidal shape having an axis of rotation 502 such that a plane generally perpendicular to the axis of rotation 502 (i.e., the plane formed by the Y axis and the Z axis, assuming the axis of rotation 502 is the X axis) intersects the patient, regardless whether the person that handholds the programmer is the patient or another person located near the patient. Stated another way, the antenna 450 is positioned relative to the ground plane 462 such that maximum RF radiation and maximum gain of the antenna are generally directed toward the patient within which the IPG is implanted, regardless whether the person that handholds the programmer is the patient or another person located near (e.g., within a few meters of) the patient. For example, when a programming person is within a few meters of and faces toward a patient within which an IPG is implanted, and the programming person handholds the programmer 422 in its intended orientation, there is maximum RF radiation and maximum gain generally directed toward the patient within which an IPG is implanted. Similarly, when the patient within which the IPG is implanted holds the programmer 422 in its intended orientation, there is also maximum RF radiation and maximum gain generally directed toward the patient.

Explained in a slightly different manner, the antenna is positioned relative to the ground plane such that the radiation pattern produced by the antenna has a generally toroidal shape having an axis of rotation generally parallel to the width of the programmer, where the width extends between left and right sides of the programmer.

Figure 1A:
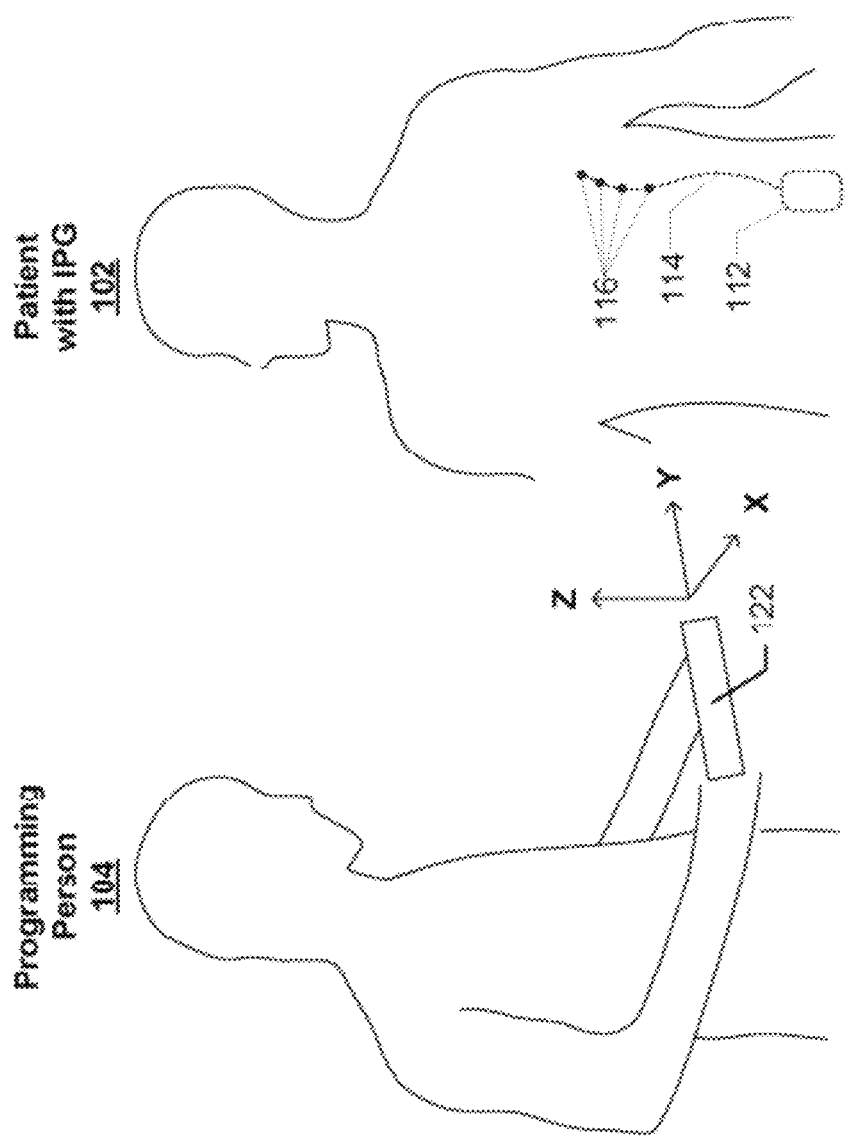
FIG. 1A illustrates how a programming person may handhold an external programmer, e.g., a clinician programmer, when using the external programmer to program an IPG implanted within a patient.
Figure 1B:
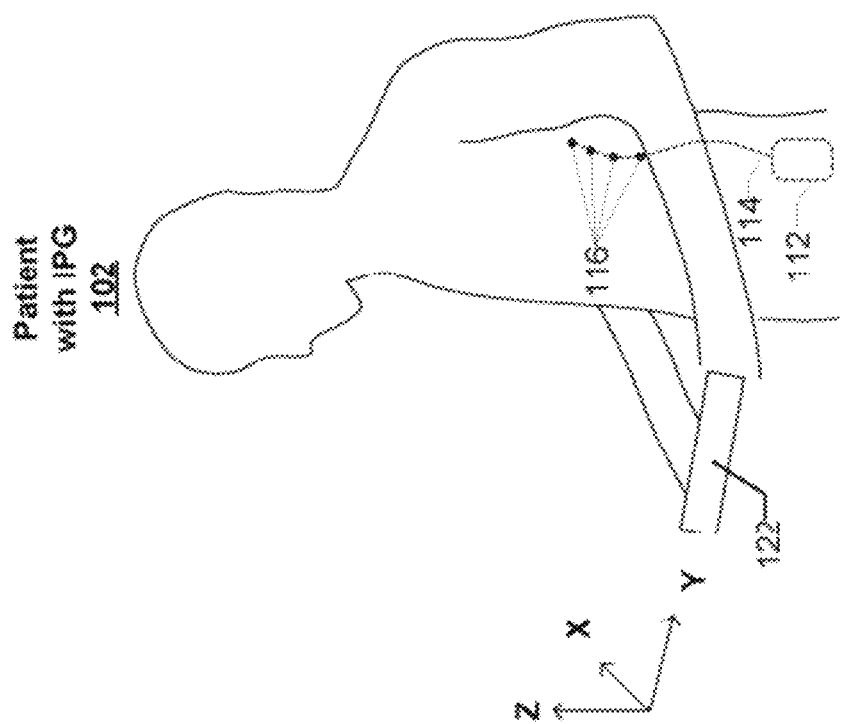
FIG. 1B illustrates how a patient may handhold an external programmer, e.g., a patient programmer, when using the external programmer to select a neurostimulation parameter set or adjust a neurostimulation parameter stored in the IPG implanted within the patient.
Figure 1C:
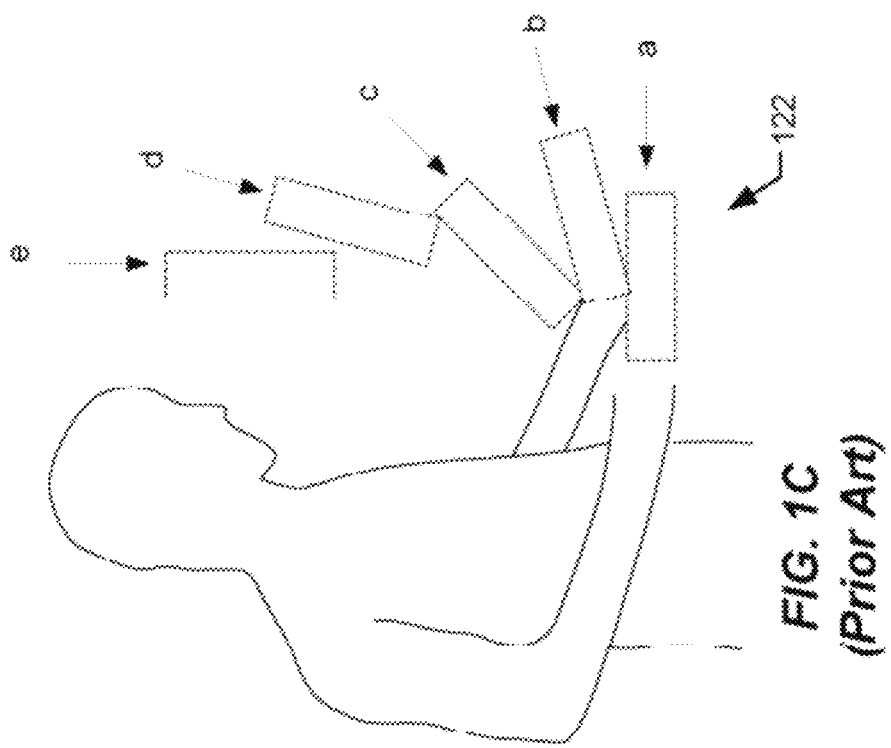
FIG. 1C illustrates how an external programmer can be in its predetermine intended orientation when a person handholds the programmer such that the front surface of the housing is at any angle between and inclusive of parallel to the earth's surface and perpendicular to the earth's surface, which enables the person to view and interact with a user interface of the programmer in the predetermined intended manner.

It can also be appreciated from FIG. 5B that if the programmer 422 (and thus its ground plane 462) is rotated about the axis 502 such that a face of the programmer is at any angle between and inclusive of parallel to the earth's surface and perpendicular to the earth's surface (e.g., similar to as shown in FIG. 1C), the antenna radiation pattern remains the same. The importance of the improved antenna radiation pattern shown in FIG. 5B, for use in communicating with an IPG, is compounded by the fact that maximum EIRP allowed by the MICS standard is only 25 microwatts.

It may be appreciated that although in FIGS. 4, 5A and 5B the antenna 450 is shown as a straight wire, the antenna may have other shapes which form substantially the same radiation pattern. For example, the antenna may have a curved, sinusoidal, zigzag regular, or irregular shape, to name a few. This is because the shape of the antenna mainly dictates the length of the antenna 450, which affects the frequency of signals emitted by the antenna, but not the radiation pattern. It is the location of the antenna relative to the ground plane which dictates the radiation pattern. As will be described below, the radiation pattern of the present invention can more generally be achieved by placement of the antenna to the side(s) of one or both of the side (i.e., left and/or right) boundaries of the ground plane. In other words, substantially the same radiation pattern as shown in FIG. 5B can also be achieved when the antenna is located to the right of the right boundary of the ground plane. Substantially the same radiation pattern can also be achieved when a portion of the antenna is located to the right of the right boundary of the ground plane, and another portion of the antenna is located to the left of the left boundary of the ground plane, as will be appreciated from the following discussion.

FIGS. 6A and 6B illustrate an alternative configuration of an antenna 650 for the programmer 422. Here the antenna 650 is still to the left of the left boundary of the ground plane 462, but is no longer planar with the ground plane 462. Rather, the antenna 650 forms a loop that is generally perpendicular to the ground plane 462. Nevertheless, as can be appreciated from FIG. 6B, the antenna radiation pattern for the antenna 650 is very similar to the radiation pattern for the antenna 450 discussed with reference to FIGS. 4, 5A and 5B.

FIGS. 7A and 7B illustrate an alternative configuration of an antenna 750 for the programmer 422. Here the antenna 750 is still to the left of the left boundary of the ground plane 462, but only a portion of the antenna is planar with the ground plane 462. The remaining portion of the antenna 750 is a loop that is generally perpendicular to the ground plane 462. As can be appreciated from FIG. 7B, the antenna radiation pattern for the antenna 750 is similar to the radiation pattern for the antenna 450 discussed with reference to FIGS. 4, 5A and 5B, but slightly skewed.

FIGS. 8A and 8B illustrate an alternative configuration of an antenna 850 for the programmer 422. Here a portion of the antenna 850 is to the left of the left boundary of the ground plane 462, and a further portion of the antenna 850 is to the right of the right boundary of the ground plane 462. Both portions of the antenna 850 are loops that are generally perpendicular to the ground plane 462. Nevertheless, as can be appreciated from FIG. 8B, the antenna radiation pattern for the antenna 850 is very similar to the radiation pattern for the antenna 450 discussed with reference to FIGS. 4, 5A and 5B.

In each of the embodiments of the present invention, described with reference to FIGS. 4-8B, the antenna (e.g., 450, 650, 750 and 850) is positioned relative to the ground plane 462 such that when a person handholds the programmer 422 in its predetermined intended orientation a radiation pattern produced by the antenna (which has a generally toroidal shape) has maximum or near maximum (referred to collectively as substantially maximum) RF radiation and substantially maximum gain generally directed toward the patient, regardless whether the person that handholds the programmer is the patient within which the IPG is implanted or another person (e.g., a programming person) located near the patient. This is very useful because it enables a same or similar programmer platform to be used for both a patient programmer and a clinical programmer. For example, a commonly manufactured housing, ground plane and antenna (as well as other elements) can be used to manufacture both patient programmers and clinical programmers, providing for economies of scale. If desired, the clinician programmer can nevertheless have greater programming capabilities than the patient programmer despite having the same or similar hardware.

In FIGS. 4-8B, the ground plane 462 was shown as having a left boundary, a right boundary, a top boundary and a bottom boundary, which collectively form a substantially planar outer boundary of the ground plane 462. In the embodiments shown in FIGS. 4-8B, the antenna does not extend beyond the top boundary of the ground plane or beyond the bottom boundary of the ground plane so as to achieve a maximal antenna radiation pattern. If the antenna were to extend beyond the top and/or bottom boundary of the ground plane the radiation pattern would start to rotate in a manner that would reduce the efficiency and effectiveness for communications with an IPG. For an extreme example, if the entire antenna were to extend beyond the top and/or bottom boundary of the ground plane, the antenna radiation pattern shown in and described with reference to FIG. 3B would result. Nevertheless, in accordance with certain embodiments of the present invention, a less than maximal but acceptable antenna radiation pattern may be achieved if significantly all (e.g., at least 80 or 90%) of the antenna remained to the left and/or right of the outer boundary of the ground plane 462. For example, a less than maximal but acceptable antenna radiation pattern may be achieved if no more than 10% of the antenna extends beyond the top boundary of the ground plane, and no more than 10% of the antenna extends beyond the bottom boundary of the ground plane.

Referring back to FIG. 4, in accordance with specific embodiments the ground plane 462 is a conductive (e.g., copper or metal) surface on a printed circuit board (PCB) 454 located within the housing 452. In such embodiments, if the antenna is planar with the ground plane, the antenna can be a conductive trace on the same PCB as the ground plane, so long as the antenna is to the left and/or right of the outer boundary of the ground plane. Such an antenna, which is printed on a PCB, is sometimes referred to as a microstrip antenna. In other embodiments, the antenna can be a conductive trace on a separate PCB. The separate PCB on which the antenna is located can be planar with the PCB on which the ground plane is located. In another embodiment, the second PCB on which the antenna is located can be perpendicular to the PCB on which the ground plane is located. This latter embodiment is beneficial because it allows for the area of the ground plane to be maximized, with provides for maximum stability for the antenna. Other angles between the two PCBs are also possible, and within the scope of the present invention. In an embodiment, the PCB can have two rigid portions that are connected by a flexible portion of the PCB, with the ground plane located on one of the rigid portions and the antenna located on the other rigid portion. In such an embodiment, the flexible portion of the PCB enables the antenna and the ground plane to be located on the same PCB, yet be at an angle relative to one another. In a further embodiment, the entire PCB can be flexible, with the ground plane on one portion of the flexible PCB and the antenna located on another portion of the flexible PCB. In still other embodiments, the antenna need not be a conductive trace on a PCB, but instead can be a conductive wire antenna, a conductive strip of metal antenna, or a slotted antenna, but is not limited thereto.

In each of the above described embodiments, the antenna was described as being within the housing of the programmer, within which the ground plane is also located. In alternative embodiments, so long as the antenna is still located relative to the ground plane such that the desired radiation pattern (e.g., initially described with reference to FIG. 5B) is achieved, the antenna can be located outside of the housing within which is located the ground plane. In still another embodiment, the antenna can be built directly into or onto the housing, e.g., by manufacturing a conductive trace on the inner and/or outer surface of the housing. In other words, the antenna can be integrally formed with the housing.

Figure 9:
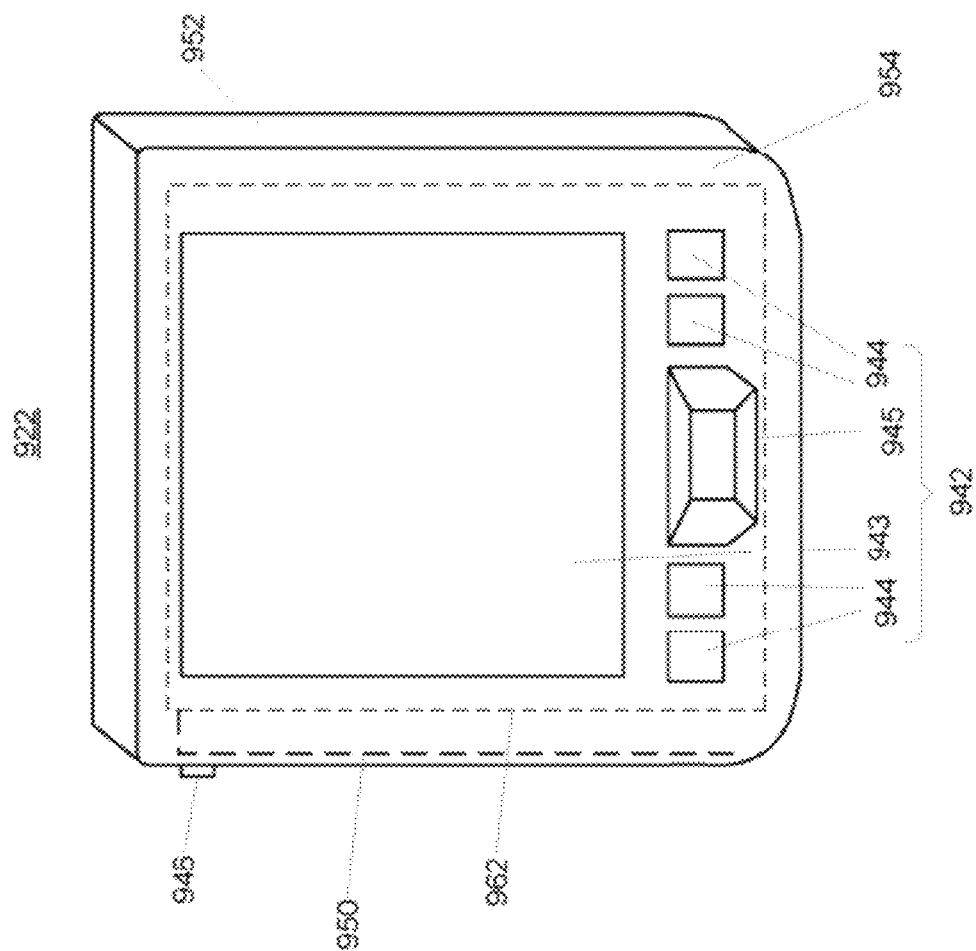
FIG. 9 illustrates an exemplary form factor for an external handheld programmer according to an embodiment of the present invention.

FIG. 9 illustrates an exemplary form factor for a programmer 922 (e.g., 422), according to an embodiment of the present invention, which can be used as a clinician programmer or a patient programmer. The programmer is shown as including a housing 952 (e.g., 452) within which electrical components of the programmer are located, some of which are described in more detail with reference to FIG. 10 below. The front surface 954 of the programmer 922, which is the front of the housing 952 in this example, is shown as including or otherwise having associated with it a user interface 942 that includes a display 943 (which may or may not be a touch screen type display), buttons 944, and a pointing device 945 that can be used like a mouse to move a cursor and/or make selections. An on/off switch 946 is shown as extending from a left surface of the housing 952. Shown in dashed lines within the housing 952 are a ground plane 962 (e.g., 462, 662, 762 or 862, but not limited thereto) and an antenna 950 (e.g., 450, 650, 750 or 850, but not limited thereto) and their relative locations to one another. The ground plane 962 acts as ground reference for the antenna and the circuitry described below with reference to FIG. 10.

Figure 10:
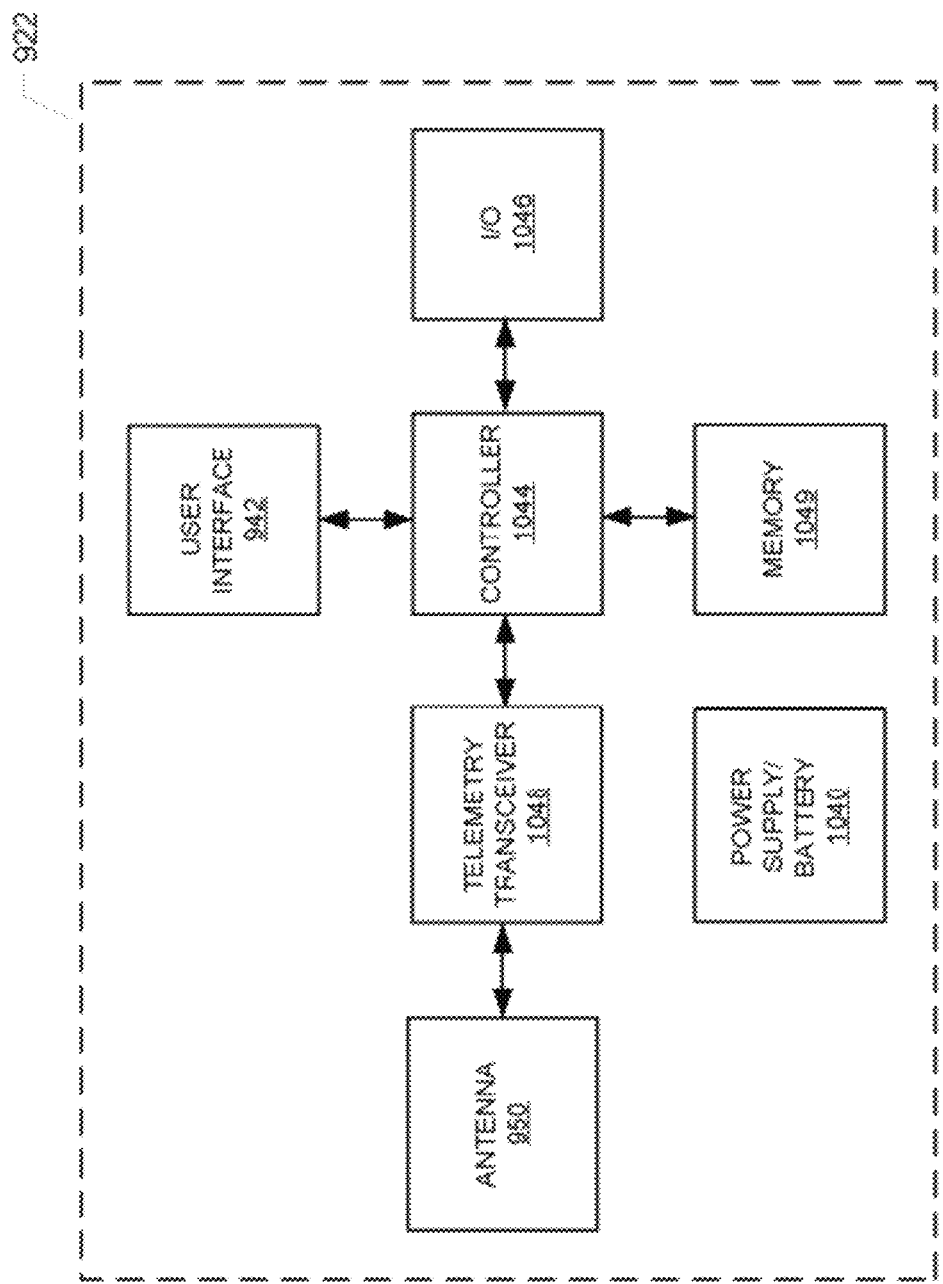
FIG. 10 is a simplified block diagram that illustrates possible components of the external handheld programmer of FIG. 9 according to an embodiment of the present invention.

FIG. 10 is a simplified block diagram that illustrates possible components of the exemplary programmer 922 (e.g., 422), according to an embodiment of the present invention. Referring to FIG. 10, in addition to the user interface 942, the external programmer 922 is shown as including a controller 1044, input and output (I/O) circuitry 1046, a telemetry transceiver 1048 and memory 1049. All such circuitry can be grounded by the ground plane 962 discussed above. The external programmer is also shown as including a power supply 1040 and the antenna 950.

The power supply 1040, which can include a battery, can be used to power the various other components of the external programmer 922. As such, the power supply 1040 can be coupled to the user interface 942, the controller 1044, the input and output (I/O) circuitry 1046, the telemetry transceiver 1048 and the memory 1049. The power supply 1040 can include, e.g., a voltage regulator (not shown) to step up or step down a voltage provided by a battery or an external power source to produce one or more predetermined voltages useful for powering such components of the external programmer 922.

The telemetry transceiver 1048 can be electrically connected to the antenna 950 by a coaxial cable or other transmission line. The telemetry transceiver 1048 can include any well known circuitry for transmitting signals via the antenna 950 to a telemetry transceiver within an IPG, as well as for receiving signals via the antenna 950 from an IPG. Such transceivers are available, e.g., from companies such as Zarlink Semiconductor Inc., headquartered in Ottawa, Canada. The antenna 950 can be any antenna according to an embodiment of the present invention, including, but not limited to antennas 450, 650, 750 and 850.

A programming person or patient may interact with the controller 1044 via the user interface 952 in order to test various neurostimulation parameter sets, input user feedback, select preferred or optimal programs, and the like. Exemplary details of the user interface 952 were provided above, but embodiments of the present invention are not limited to these exemplary details.

The controller 1044 can include a microprocessor, a microcontroller, a digital signal processor (DSP), an application specific integrated circuit (ASIC), a field-programmable gate array (FPGA), a state machine, or similar discrete and/or integrated logic circuitry. The I/O circuitry 1046 can include transceivers for wireless communication, ports for wired communication and/or communication via removable electrical media, and/or appropriate drives for communication via removable magnetic or optical media. The controller 1044 can, e.g., collect information relating to tested electrode parameters (e.g., combinations) and neurostimulation signal parameters, and store the information in the memory 1049 for later retrieval and review by a clinician, physician or by the controller 1044 to facilitate identification of one or more preferred neurostimulation parameter sets. The controller 1044 can send instructions to the IPG 112 via the telemetry circuit 1048 to cause the testing of various neurostimulation parameter sets. For example, the controller 1044 can effectuate the testing of neurostimulation parameter sets created by the controller 1044 or a programming person to the IPG 112.

The memory 1049 can include program instructions that, when executed by the controller 1044, cause the programmer 922 to perform at least some of the functions described herein. For example, the controller 1044 can execute program instructions that specify protocols for testing various neurostimulation parameter sets and selecting one or more preferred neurostimulation parameter sets. The memory 1049 can also store one or more neurostimulation parameter sets determined to treat targeted pain for a patient, along with information about the patient. The memory 1049 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Embodiments of the present invention are also directed to methods for using the programmers described herein to communicate with an IPG implanted within a patient. For example, such a method can include using a programmer to communicate with an IPG implanted within a patient, where the antenna of the programmer is positioned relative to a ground plane of the programmer so that substantially maximum RF radiation and substantially maximum gain of the antenna is generally directed toward the patient within which the IPG is implanted, when the programmer is handheld in its intended orientation by the patient or another person near the patient. Additionally, embodiments of the present invention are also directed to methods for manufacturing or otherwise providing programmers that achieve the improved antenna radiation pattern described herein. For example, such a method can include manufacturing a programmer that includes a ground plane and an antenna positioned relative to one another so that the antenna is to the left of and/or the right of an outer boundary of the ground plane when the programmer is handheld in its intended orientation. Further, embodiments of the present invention are also directed to systems that incorporate the programmers described herein.

While embodiments of the present invention are especially useful when used to transmit data in accordance the MICS standard, embodiments of the present invention can also be used to transmit data using other medical frequency bands, e.g., including but not limited to frequency bands associated with Wireless Medical Telemetry Service (WMTS).

Before an IPG is implanted within a patient to deliver a therapy, a non-implanted pulse generator device that replicates some or all of the IPG functions can be connected to the patient to evaluate the efficacy of the proposed therapy. Such a non-implanted device is often referred to as a trial neurostimulator (TNS) device. The TNS device can be taped to a patient's back, hooked on a patient's belt, or attached to the patient in some other manner. It is also possible that a non-implanted pulse generator device, similar to a TNS, can be used for extended periods of time, in which case the non-implanted device may no longer qualify as a "trial" device. When using such a TNS or other non-implanted pulse generator device, stimulation lead(s) that extend from a non-implanted housing or header of the device can be inserted into the patient (e.g., percutaneously) so that distal portions of the lead(s) are positioned at appropriate locations, e.g., along the spinal cord. The same handheld external programmers of embodiments of the present invention (which were described above as communicating with an IPG) can also be used to communicate wirelessly with such a TNS or other non-implanted pulse generator. In other words, the programmers of embodiments of the present invention are not limited to use with implantable pulse generators.

In each of the above described embodiments, the programmer was generally described as having a single predetermined intended orientation that specifies how a person should handhold the programmer so that the person can view and interact with a user interface of the programmer in a predetermined intended manner. As was explained in great detail above, in such embodiments, a preferred antenna radiation pattern is achieved by locating the antenna relative to the ground plane such that the entire antenna (or at least, substantially the entire) antenna is located left of an outer boundary of the ground plane and/or right of the outer boundary of the ground plane. This results in the radiation pattern produced by the antenna having substantially maximum radio frequency (RF) radiation generally directed toward the patient, regardless whether the person that handholds the programmer is the patient or another person located near the patient.

Figure 11:
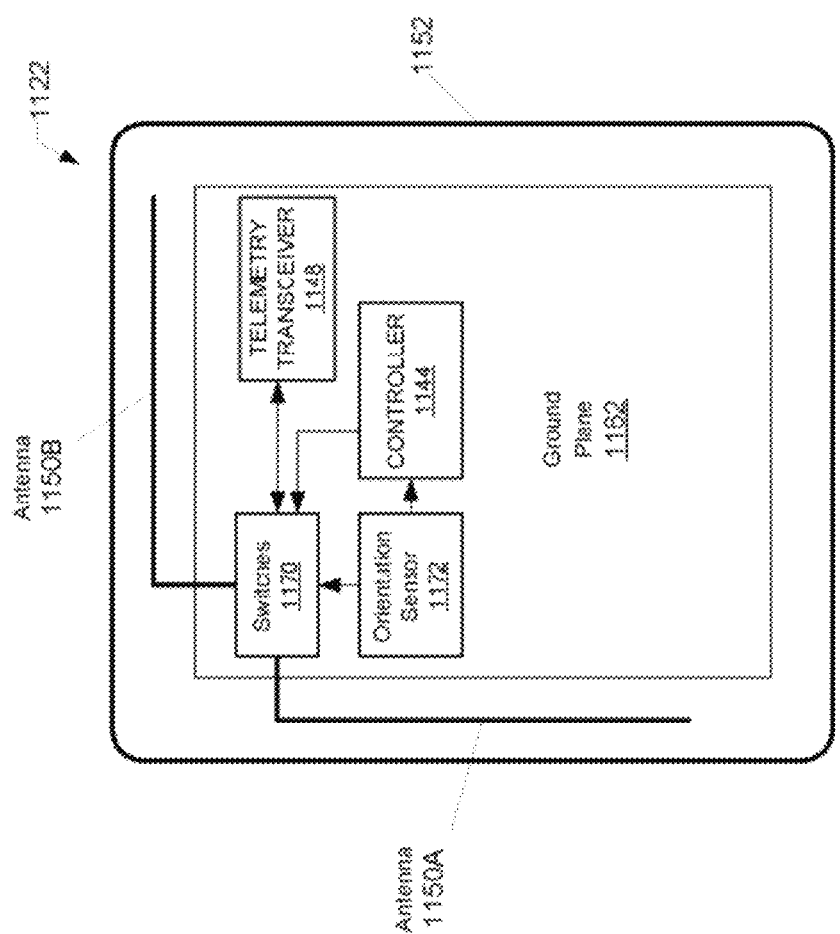
FIG. 11 illustrates a programmer that includes two separate antennas, one of which is selected for use at a time, in accordance with an embodiment of the present invention.

In alternative embodiments, described with reference to FIG. 11, a programmer can have two predetermined intended orientations, including a portrait orientation (where the programmer is oriented such that its height is greater than its width) and a landscape orientation (where the programmer is oriented such that its width is greater than its height). In FIG. 11, the programmer 1122 is shown as being in its portrait orientation. The programmer 1122 can be placed in its landscape orientation, e.g., by rotating the programmer counterclockwise by 90 degrees.

As shown in FIG. 11, the programmer 1102 can include an orientation sensor 1172 that can detect whether the programmer is being held in its portrait orientation or its landscape orientation. Such an orientation sensor 1172 can be, e.g., an accelerometer or gravitometer, but is not limited thereto. Numerous orientation sensors are commercially available and are often used in smart phones and tablet computing devices to detect the orientation of the phone/device, so that a screen (e.g., a touch screen) or other user interface of the phone/device can be oriented to match the orientation of the phone/device.

In a similar manner as is done in smart phones and other devices, information (e.g., provided in the form of digital and/or analog signals) from the orientation sensor 1172 can be used to appropriately orient a touch screen and/or other user interface of the programmer 1122. Additionally, in accordance with an embodiment of the present invention, information from the orientation sensor 1172 can be used to select among at least two antennas, so that the preferred antenna radiation pattern can be achieved regardless whether the programmer 1122 is being held in its portrait orientation or its landscape orientation.

Referring to FIG. 11, the orientation sensor 1172 can provide information indicative of the orientation of the programmer 1122 to a controller 1144 (similar to controller 1044), and the controller 1144 can control switches 1170 to select use of either antenna 1150A or antenna 1150B. More specifically, when the orientation sensor 1172 indicates that the programmer 1122 is in its portrait orientation, the controller 1144 can control the switches 1170 so that the antenna 1150A is connected to the telemetry transceiver 1148 (similar to transceiver 1048), which results in the connected antenna being to the side (i.e., left side) of the outer boundary of the ground plane 1162. When information from the orientation sensor 1172 indicates that the programmer 1122 is in its landscape orientation, the controller 1144 can control the switches 1170 so that the antenna 1150B is connected to the telemetry transceiver 1148, which again results in the connected antenna being to the side (i.e., left side) of the outer boundary of the ground plane 1162. The relative location of the antenna 1150B to the ground plane 1162 when the programmer 1122 is in its landscape orientation can be appreciated by rotating FIG. 11 counterclockwise by 90 degrees. It is also possible that the orientation sensor 1172 directly controls the switches 1170, rather than requiring that the controller 1144 controls the switches.

The antennas 1150A and 1150B, which are shown as being relatively perpendicular to one another, can be located within, outside and/or integral with the housing 1152. By selecting the appropriate antenna 1150A or 1150B, the radiation pattern produced by the selected antenna can have substantially maximum radio frequency (RF) radiation generally directed toward the patient, regardless of whether the programmer is in its portrait or landscape orientation, and regardless whether the person that handholds the programmer is the patient or another person located near the patient.

When a programming person uses an external programmer to program a pulse generator, it is preferred that the programming person and the patient face one another (i.e., are face to face) so that the programming person can observe the facial expressions and visual cues as to the stimulation being perceived by the patient during the programming process. Embodiments of the present invention provide for improved communications during such a face to face programming process.

While preferred embodiments of the present invention have been shown and described herein, those skilled in the art will appreciate that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A handheld external programmer adapted to wirelessly communicate with an implantable pulse generator (IPG) implanted within a patient or an external pulse generator attached to the patient,
the programmer having a predetermined intended orientation that specifies how a person should handhold the programmer so that the person can view and interact with a user interface associated with a front surface of the programmer in a predetermined intended manner,
wherein when the person handholds the programmer in its predetermined intended orientation, the front surface of the housing is positioned at any angle between and inclusive of the front surface facing upward parallel to the earth's surface and the front surface facing sideways perpendicular to the earth's surface, which enables the person to view and interact with the user interface of the programmer in the predetermined intended manner,
the external programmer comprising:
a ground plane;
a power supply;
a telemetry transceiver powered by the power supply and grounded by the ground plane; and
only a single antenna electrically connected to the telemetry transceiver;
wherein the single antenna is positioned relative to the ground plane such that when the person handholds the programmer in its predetermined intended orientation a single radiation pattern produced by the antenna has substantially maximum radio frequency (RF) radiation generally directed toward the patient, regardless whether the person that handholds the programmer in its predetermined intended orientation is the patient or another person located near and generally facing the patient, and without requiring the programmer be placed over the pulse generator.

2. The handheld external programmer of claim 1, wherein the ground plane comprises a conductive surface on a printed circuit board (PCB).

3. The handheld external programmer of claim 2, wherein the single antenna comprises a conductive trace on a printed circuit board (PCB).

4. The handheld external programmer of claim 3, wherein the PCB on which is the conductive trace of the single antenna is separated from the PCB on which is the conductive surface of the ground plane.

5. The handheld external programmer of claim 4, wherein the PCB on which is the conductive trace of the single antenna is substantially perpendicular to the PCB on which is the conductive surface of the ground plane.

6. The handheld external programmer of claim 3, wherein the PCB on which is the conductive trace of the single antenna is the same as the PCB on which is the conductive surface of the ground plane.

7. The handheld external programmer of claim 1, further comprising a housing within which is located the ground plane, the power supply and the telemetry transceiver.

8. The handheld external programmer of claim 7, wherein the single antenna is located within the housing.

9. The handheld external programmer of claim 7, wherein the single antenna is located outside the housing or integral with the housing such that when a person handholds the programmer in its predetermined intended orientation the single antenna is adjacent the left side or right side of the housing.

10. The handheld programmer of claim 1, wherein the single antenna is positioned relative to the ground plane such that when the person handholds the programmer in its predetermined intended orientation the single radiation pattern produced by the single antenna has a generally toroidal shape having an axis of rotation such that a plane generally perpendicular to the axis of rotation intersects the patient, regardless whether the person that handholds the programmer in its predetermined intended orientation is the patient or another person located near and generally facing the patient, and without requiring the programmer be placed over the pulse generator.

11. The handheld programmer of claim 1, wherein:
the programmer has a width extending between left and right sides of the programmer when the programmer is held in its predetermined intended orientation;
the ground plane is substantially planar and has a left boundary, a right boundary, a top boundary and a bottom boundary, which collectively form a substantially planar outer boundary of the ground plane; and
when the programmer is in its predetermined intended orientation, substantially the entire single antenna is located between the left boundary of the ground plane and the left side of the programmer or between the right boundary of the ground plane and the right side of the programmer, and the single radiation pattern produced by the antenna has a generally toroidal shape having an axis of rotation generally parallel to the width of the programmer.

12. The handheld external programmer of claim 1, wherein:
the ground plane is substantially planar and has a left boundary, a right boundary, a top boundary and a bottom boundary, which collectively form a substantially planar outer boundary of the ground plane; and
when the person handholds the programmer in its predetermined intended orientation, substantially the entire single antenna is located left of the outer boundary of the ground plane or right of the outer boundary of the ground plane.

13. The handheld external programmer of claim 1, wherein when the person handholds the programmer in its predetermined intended orientation:
the ground plane has a left boundary, a right boundary, a top boundary and a bottom boundary, which collectively form a substantially planar outer boundary of the ground plane;
substantially the entire single antenna is located left of the left boundary of the ground plane-or right of the right boundary of the ground plane;
the single antenna does not extend substantially beyond the top boundary of the ground plane; and
the single antenna does not extend substantially beyond the bottom boundary of the ground plane.

14. The handheld external programmer of claim 1, wherein when the person handholds the programmer in its predetermined intended orientation:
the ground plane has a left boundary, a right boundary, a top boundary and a bottom boundary, which collectively form a substantially planar outer boundary of the ground plane;
substantially the entire single antenna is located left of the left boundary of the ground plane or right of the right boundary of the ground plane;
no more than 10% of the single antenna extends beyond the top boundary of the ground plane; and
no more than 10% of the antenna extends beyond the bottom boundary of the ground plane.

15. The handheld external programmer of claim 1, wherein the single antenna is selected from the group consisting of:
   a conductive wire antenna;
   a conductive strip of metal antenna;
   a slotted antenna; and
   a microstrip antenna.

* * * * *